(12) United States Patent
Olsson et al.

(10) Patent No.: US 7,250,178 B2
(45) Date of Patent: Jul. 31, 2007

(54) ANTIMICROBIAL CERAMIC GLAZE

(75) Inventors: Anders Olsson, Satofta (SE); Howard Wayne Swofford, Newton, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 11/040,379

(22) Filed: Jan. 21, 2005

(65) Prior Publication Data
US 2005/0158400 A1 Jul. 21, 2005

Related U.S. Application Data

(60) Provisional application No. 60/567,671, filed on May 3, 2004, provisional application No. 60/538,074, filed on Jan. 21, 2004.

(51) Int. Cl.
*A01N 59/16* (2006.01)
*C03C 3/14* (2006.01)
*C03C 8/00* (2006.01)
*C03C 8/04* (2006.01)

(52) U.S. Cl. .................... 424/641; 424/409; 424/411; 501/14; 501/26; 501/49; 106/419; 106/425

(58) Field of Classification Search ........ 424/618–619, 424/630, 632–635, 637, 641; 501/14, 26, 501/49; 106/419, 425
See application file for complete search history.

(56) References Cited

U.S. PATENT DOCUMENTS 3,812,229 A 5/1974 Anderson .................... 264/60
2003/0030042 A1* 2/2003 Sawada et al. ............. 252/604

OTHER PUBLICATIONS

Jackson, William M., "Low Firing Glazes and Slips," Ceramic Bulletin, vol. 68 (1), 1989, pp. 87-88.*
HCAPLUS Abstract 1996:48411 (1996).*
Derwent Abstract 1998-525403 (1998).*
Derwent Abstract 1994-188732 (1994).*
Japanese Industrial Standard, JIS Z 2801:2000, Antimicrobial Products—Test for Antimicrobial Activity and Efficacy.

* cited by examiner

*Primary Examiner*—John Pak
(74) *Attorney, Agent, or Firm*—Cliff D. Weston

(57) ABSTRACT

An antimicrobial ceramic glazing composition comprising zinc borate for imparting antimicrobial characteristics to numerous ceramic products. A method for producing the antimicrobial glazing composition and ceramic products incorporating the antimicrobial glazing composition.

7 Claims, No Drawings

ANTIMICROBIAL CERAMIC GLAZE

CROSS-REFERENCE TO RELATED APPLICATIONS

This application is entitled to the benefit of, and claims priority to provisional U.S. Patent Application Ser. No. 60/538,074, filed on Jan. 21, 2004, and provisional U.S. Patent Application Ser. No. 60/567,671, filed on May 3, 2004, each of which is incorporated herein by reference in its entirety.

FIELD OF THE INVENTION

The present invention relates to the field of antimicrobial protection. More specifically, the present invention relates to a composition for imparting built-in and long lasting antimicrobial characteristics to ceramic products. In particular, the present invention pertains to ceramic glazing compositions that impart built-in antimicrobial characteristics to ceramic products.

BACKGROUND OF THE INVENTION

The field of providing products with built-in antimicrobial protection has grown tremendously over the past several years. What once started out as a premium or novel option for high-end consumer products and medical devices has now grown into a mainstream characteristic found in many consumer products. Consumers can go to any home improvement center and see dozens if not hundreds of products that claim some degree of resistance to microbiological growth or contamination. Some major retailers have specific sections devoted to such antimicrobial products.

Antibacterial products have been introduced into plastics, textiles, liquids, metal coatings, and an array of other types of materials. However, there remain several areas of consumer and commercial products in which development of commercially viable antimicrobial products has proven difficult. One such area is ceramic coatings.

Ceramic coatings are commonly used in products that store, treat, or transport water and liquid waste. Ceramic toilets, urinals, bidets, bathroom basins, flooring tiles and other bathroom fixtures are probably the most common example of such products.

Ceramic products used to collect and transport water are often stained by scum and films of biologic origin (e.g., bacteria, fungus, mold, mildew). To date, the primary method of removing biological scum and film from these ceramic products has been to abrade the ceramic surface in the presence of topical cleaning agent. This process is time consuming and provides little or no protection against future growth. Some cleaning agents can damage the surface of the ceramic product. Therefore there is great interest in the development of ceramic coatings that have built-in protection against the growth and proliferation of microbes.

A few such built-in antimicrobial coatings are described in the ceramic literature but they have not seen commercial success. Existing technologies are somewhat limited. For example, the high temperatures used in ceramic firing processes typically preclude the use of organic antimicrobial agents. Inorganic silver-based antibacterials are too expensive. Zinc oxide is known as having antimicrobial characteristics and has been used in the preparation of ceramic glazing compositions. However, known ceramic glazing compositions that rely solely upon zinc oxide as an antimicrobial agent have not shown antimicrobial efficacy sufficient for control of microbial growth and proliferation on ceramic surfaces. Accordingly, there is a need for a low-cost ceramic coating that has built-in antimicrobial protection.

Thus, one object of the present invention is to provide a new and useful antimicrobial ceramic coating that can impart antimicrobial characteristics in a wide range of products.

A still further object of the invention is to provide this ceramic coating at a cost that is acceptable to the marketplace. Furthermore, this antimicrobial ceramic coating should be safe to humans, exhibit commercially acceptable antimicrobial properties, and most importantly, be compatible with existing ceramic production processes.

These and other objects are achieved by the claimed invention, which in one embodiment is an antimicrobial ceramic glazing composition comprising a quantity of zinc borate sufficient to achieve a commercially acceptable level of antimicrobial efficacy. In preferred embodiments this ceramic glazing composition also comprises a quantity of zinc oxide.

In a further embodiment, the invention is a ceramic article that exhibits antimicrobial properties. The ceramic article according to the invention has at least one surface and a glaze on a portion of that surface. The glaze comprises a quantity of zinc borate sufficient to achieve a commercially acceptable level of antimicrobial efficacy. In preferred embodiments this ceramic glazing composition also comprises a quantity of zinc oxide.

In yet another embodiment, the invention is a method of making an antimicrobial ceramic glaze and a method of making a ceramic article comprising the antimicrobial ceramic glaze.

DETAILED DESCRIPTION

As used herein, the terms "microbe" or "microbial" should be interpreted to encompass any of the microscopic organisms commonly studied by microbiologists. Such organisms include, but are not limited to, bacteria and fungi as well as other single-celled organisms such as mold, mildew and algae. Viral particles and other infectious agents are also included in the term microbe.

For ease of discussion, this detailed description may make reference to bacteria and antibacterial agents. This method of presentation should not be interpreted as limiting the scope of the invention in any way.

The claimed invention relates to ceramic coatings and in particular to ceramic glazing on the outer surfaces of ceramic products. The following brief discussion of vitreous china or ceramic production is provided as an aid to the reader. This discussion is presented in the context of the production of bathroom fixtures. Those skilled in the art recognize that the production process of other ceramic products may vary from that which is presented below. The claimed invention, however, is adaptable to any such variances.

The initial stage of a typical ceramic production process is the production of barbotine or slip, a clay from which bathroom ceramic products are made. Barbotine is made from a mixture of clays, kaolin, phyllites, feldspar and quartz.

Individual pieces are cast by pouring the barbotine into molds made of gypsum or microporous resin.

In the casting processes that use gypsum molds the parts are formed by absorption of water contained in the barbotine through the capillary action of the gypsum. As water leaves the barbotine the part solidifies to a point where the mold can be opened. The still malleable part is then removed from the mold.

Casting processes that use resin molds are called "high pressure" processes. Parts are formed by filtering water contained in the barbotine clay through micropores in the resin molds by the application of pressure. The water is eliminated by injecting compressed air along the molds.

Generally, gypsum molds are used for making parts with a more complex geometry and that are produced in low volumes. Resin molds are used for parts whose geometry is simpler and that are produced in high volumes.

After casting and removal from the molds, the parts go for drying in kilns under controlled humidity and temperature (approximately 90° C.). The drying cycle lasts about 7 hours, reducing the water content of the part from about 16% to less than 1%. Following this, the parts are inspected to detect possible flaws. The parts then go to the coating process. The coating process is often referred to as the enameling step or the glazing step.

The enameling step typically comprises the manual application of ceramic enamel (also called ceramic glaze) on the parts using guns in individual booths fitted with exhaust systems and water curtains. Typical ceramic glaze is produced from a mixture of kaolin, feldspar, quartz, colorings and other additives. Once coated, the parts are fired in continuous kilns, reaching temperatures of about 1,250° C., in an approximately 15-hour cycle. The firing process gives the glazed part the color and transparent appearance that is typical of vitreous china In one embodiment, the invention is a ceramic glazing composition that provides commercially acceptable antimicrobial efficacy after the firing process. In other words, the claimed glazing reduces or substantially eliminates the growth and proliferation of microbes on the surface of ceramic articles upon removal from the firing process and without any further treatment (e.g., further coating or painting of the ceramic part).

The antimicrobial ceramic glazing composition according to the invention comprises components commonly utilized in the preparation of ceramic glazing plus a quantity of zinc borate sufficient to achieve a commercially acceptable level of antimicrobial efficacy.

Zinc borate is the common term for a hydrated mineral-like substance. Zinc Borate is most often used as a flame retardant and smoke suppressant additive but it is sometimes used as an antifungal agent. However, zinc borate is not known as an antimicrobial agent in ceramic coatings.

The quantity of zinc borate required to achieve a commercially acceptable level of antimicrobial efficacy for finished ceramic products may vary depending upon the level of contamination generally associated with the product. However, the concentration of zinc borate for most commercial applications is at least about 5,000 ppm of zinc borate. Concentrations above about 100,000 ppm can have adverse impacts on the aesthetic qualities of the ceramic glaze. Concentrations of about 20,000 ppm to about 40,000 of zinc borate are preferred.

In an alternative embodiment, the glazing composition according to the invention also comprises a quantity of free zinc oxide. Free zinc oxide, as used herein, refers to an additional amount of zinc oxide that is added to the glazing composition separate from the zinc borate.

In the embodiments that employ a combination of zinc borate and zinc oxide, the weight ratio of zinc borate to zinc oxide in the glazing composition may range from about 90:10 to about 10:90. A ratio of about 50:50 is preferred but may be altered depending upon cost considerations. Preferably, a ratio of about 50:50 of zinc borate to zinc oxide is added to the ceramic glazing composition at about 2 weight % for the combination based upon the weight of the ceramic glaze composition.

Similar to the embodiment that employs zinc borate, ceramic glazing compositions comprising zinc borate and zinc oxide may have at least about 5,000 ppm of a combination of zinc borate and zinc oxide. Preferably, ceramic glazing compositions comprising a combination of zinc borate and zinc oxide have about 20,000 ppm to about 40,000 ppm of the combination. More preferably, about 20,000 ppm of the combination. Such concentrations, in varying ratios, achieved greater than a 99% reduction of microbial species applied to a ceramic surface coated with the claimed glazing composition. Concentrations above 100,000 ppm may have adverse aesthetic effects on the glazing.

If desired, other antimicrobial agents capable of surviving the high temperatures of the enameling process may be added to the glazing composition. Such agents include, but are not limited to, silver (e.g., silver salts and silver zeolites), copper, and other known metallic antimicrobial agents. Such agents can be added in relatively minor amounts to supplement biocidal activity against specific pathogens. Of course, such metallic antimicrobial agents can be added in greater quantities if desired.

In a further embodiment, the invention encompasses a ceramic article that exhibits antimicrobial properties. The claimed antimicrobial ceramic article comprises a ceramic substrate having at least one surface and a glaze on at least a portion of that surface. The glaze utilized in this embodiment of the invention is the same as that described in the first embodiment of the invention. In other words, the glaze comprises a quantity of zinc borate or a combination of zinc borate and zinc oxide that is sufficient to achieve a commercially acceptable level of antimicrobial efficacy.

In a preferred embodiment, the glazing will comprise at least about 5,000 ppm of zinc borate. Concentrations above about 100,000 ppm of zinc borate may have adverse aesthetic effects on the glazing. Concentrations of about 20,000 ppm to about 40,000 ppm of zinc borate are preferred. Alternatively, the glaze comprises a combination of zinc borate and zinc oxide, where the combined concentration of zinc borate and zinc oxide is preferably at least about 5,000 ppm Preferably, the combined concentration of zinc borate and zinc oxide is in a range of about 20,000 ppm to about 40,000 ppm. If a combination of zinc oxide and zinc borate is used, the ratio of zinc borate to zinc oxide may be about 90:10 to about 10:90, preferably about 50:50.

In a still further embodiment, the invention encompasses a method of making an antimicrobial ceramic glaze and an article having an antimicrobial ceramic glaze.

The antimicrobial ceramic glaze according to the invention may be made by adding zinc borate or a combination of zinc borate and zinc oxide, both of which are commercially available from a number of sources, to an existing glazing composition. Those skilled in the art of preparing glazing compositions will recognize that the zinc borate and zinc oxide may be added separately or in combination at any point in the process of making the glazing composition.

Of course, care should be taken to ensure that the quantity of zinc borate (or a combination of zinc borate and zinc oxide) is sufficient to achieve a commercially acceptable level of antimicrobial efficacy. In preferred embodiments the quantities of these antimicrobial agents are the same as those set forth above in the discussion of the glazing composition.

The method of making the claimed antimicrobial ceramic article closely resembles the general method for making ceramic articles set forth at the beginning of the detailed description. However, in the method according to the invention, upon removal of the article from the mold, the article is coated with the antimicrobial ceramic glazing composition according to the invention. The coated article is then fired as usual with the ceramic coating retaining its antimicrobial characteristics even after the firing.

EXAMPLES

Several ceramic articles were prepared to test the antimicrobial characteristics of the recited glaze which comprises a combination of zinc borate and zinc oxide. The test articles comprised an underlying ceramic substrate made from a standard commercial barbotine. The glaze used in the testing was a standard glaze comprising silica sand, feldspar, calcium carbonate, china clay, zirconium silicate, a small amount of CMC as a binder, and a small amount of zinc oxide. To this basic glaze composition was added varying quantities of zinc borate and zinc oxide. The glaze composition according to the invention was applied to the articles by spraying. The articles were then fired at 1200° C. One test article was prepared without any additional zinc oxide or zinc borate for use as a control.

Six samples and one control were prepared in accordance with the following table.

| Sample | Antimicrobial Concentration in the Glaze | Ratio of Zinc Borate to Zinc Oxide |
| --- | --- | --- |
| 1 | 20,000 ppm | Zinc Borate:Zinc Oxide-90:10 |
| 2 | 40,000 ppm | Zinc Borate:Zinc Oxide-90:10 |
| 3 | 20,000 ppm | Zinc Borate:Zinc Oxide-50:50 |
| 4 | 40,000 ppm | Zinc Borate:Zinc Oxide-50:50 |
| 5 | 20,000 ppm | Zinc Borate:Zinc Oxide-10:90 |
| 6 | 40,000 ppm | Zinc Borate:Zinc Oxide-10:90 |
| 7 (control) | 0 ppm | Standard Glaze which includes some zinc oxide. |

These six samples were tested in accordance with Japanese Industrial Standard Z 2801:2000, one of the most common test methods for antibacterial efficacy in inorganic ingredients. The organism utilized in the test was *E. coli*, which is a pathogenic microbe commonly found in human feces, and therefore also commonly found on toilets and other bathroom products. Test results are reported as a percent reduction of bacteria.

| Sample | Bacteria on Control after 24 hours | Bacteria on Sample after 24 hours | Relative Reduction of Bacteria |
| --- | --- | --- | --- |
| 1 | $5.4 \times 10^5$ | $<1.0 \times 10^2$ | >99.98 |
| 2 | $5.4 \times 10^5$ | $<1.0 \times 10^2$ | >99.98 |
| 3 | $5.4 \times 10^5$ | $<1.0 \times 10^2$ | >99.98 |
| 4 | $5.4 \times 10^5$ | $<1.0 \times 10^2$ | >99.98 |
| 5 | $5.4 \times 10^5$ | $<1.0 \times 10^2$ | >99.98 |
| 6 | $5.4 \times 10^5$ | $<1.0 \times 10^2$ | >99.98 |
| 7 (control) | $5.4 \times 10^5$ | $5.4 \times 10^5$ | 0 |

The above results demonstrate that the glaze according to the invention showed commercially acceptable efficacy against *E. coli* relative to the control.

As noted previously, the ceramic glaze according to the invention was designed to impart built-in antimicrobial protection to a variety of ceramic articles. Accordingly, the scope of the invention includes ceramic articles that incorporate the glazing according to the invention. Such articles include, but are not limited to, toilets, bidets, washbasins, towel rails, soap holders, toilet roll holders, water control fixtures (e.g., hot and cold water handles), ceramic tiles, and other ceramic applications.

What is claimed is:

1. An antimicrobial ceramic glazing composition, comprising:
   zinc borate; and
   an additional quantity of free zinc oxide;
   wherein the antimicrobial ceramic glazing composition has a combined concentration of zinc borate and free zinc oxide of from at least about 5,000 ppm to about 40,000 ppm; and
   wherein the antimicrobial ceramic glazing composition has a weight ratio of zinc borate to free zinc oxide from about 10:90 to about 90:10.

2. a ceramic article comprising the antimicrobial ceramic glazing compositing according to claim 1.

3. The ceramic article according to claim 2 wherein the ceramic article is selected from the group consisting of toilets, bidets, washbasins, towel rails, soap holders, toilet roll holders, water control fixtures, and ceramic tiles.

4. A ceramic article exhibiting built-in antimicrobial properties, comprising:
   a ceramic substrate having at least one surface; and
   a glaze on at least a portion of said surface;
   wherein said glaze includes a quantity of zinc borate and an additional quantity of free zinc oxide having a weight ratio of zinc borate to free zinc oxide from about 10:90 to about 90:10; and
   wherein the antimicrobial ceramic glazing composition has a combined concentration of zinc borate and free zinc oxide of from at least about 5,000 ppm to about 40,000 ppm.

5. The ceramic article according to claim 4, wherein the ceramic article is selected from the group consisting of toilets, bidets, washbasins, towel rails, soap holders, toilet roll holders, water control fixtures, and ceramic tiles.

6. A method for forming a ceramic glaze having built-in antimicrobial properties, the method comprising:
   providing a ceramic substrate having at least one surface;
   coating a ceramic glazing composition on at least a portion of said surface; and
   firing the ceramic glazing composition;
   wherein the ceramic glazing composition includes a quantity of zinc borate and an additional quantity of free zinc oxide having a weight ratio of zinc borate to free zinc oxide from about 10:90 to about 90:10; and
   wherein the antimicrobial ceramic glazing composition has a combined concentration of zinc borate and free zinc oxide of from at least about 5,000 ppm to about 40,000 ppm.

7. The method according to claim 6, wherein the fired coated substrate is selected from the group consisting of toilets, bidets, washbasins, towel rails, soap holders, toilet roll holders, water control fixtures, and ceramic tiles.

* * * * *